US011872054B2

United States Patent
Medeiros

(10) Patent No.: US 11,872,054 B2
(45) Date of Patent: Jan. 16, 2024

(54) PHYSIOLOGICAL SENSOR AND SENSING METHOD WITH SENSOR LIFT DETECTION

(71) Applicant: GE Precision Healthcare LLC, Wauwatosa, WI (US)

(72) Inventor: Daniel W. Medeiros, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 300 days.

(21) Appl. No.: 16/890,834

(22) Filed: Jun. 2, 2020

(65) Prior Publication Data

US 2021/0369205 A1 Dec. 2, 2021

(51) Int. Cl.
*A61B 5/00* (2006.01)
*A61B 5/01* (2006.01)

(52) U.S. Cl.
CPC .......... *A61B 5/6844* (2013.01); *A61B 5/0008* (2013.01); *A61B 5/01* (2013.01); *A61B 5/746* (2013.01); *A61B 2503/045* (2013.01)

(58) Field of Classification Search
CPC ....... A61B 5/6844; A61B 5/0008; A61B 5/01; A61B 5/746
See application file for complete search history.

(56) References Cited

U.S. PATENT DOCUMENTS

| | | |
|---|---|---|
| 2008/0183029 A1 | 7/2008 | Mackin |
| 2016/0022398 A1* | 1/2016 | Vetter .................... A61B 5/053 433/27 |
| 2016/0192885 A1* | 7/2016 | Lee ...................... A61B 5/6841 600/300 |
| 2017/0095214 A1* | 4/2017 | Ramachandran ...... A61B 5/053 |
| 2017/0259015 A1 | 9/2017 | Caspers |
| 2017/0347910 A1* | 12/2017 | Shochat ................ A61B 5/276 |
| 2018/0084667 A1 | 3/2018 | Saeidi |
| 2018/0168508 A1* | 6/2018 | Biel ...................... A61B 5/6843 |
| 2019/0223806 A1* | 7/2019 | Bennet ................... A61B 5/282 |

OTHER PUBLICATIONS

International Application No. PCT/US2021/035183 filed Jun. 1, 2021—International Search Report and Written Opinion dated Sep. 15, 2021; 19 pages.

* cited by examiner

*Primary Examiner* — Daniel L Cerioni
(74) *Attorney, Agent, or Firm* — Andrus Intellectual Property Law, LLP

(57) ABSTRACT

A physiological sensor includes a sensing element to detect physiological information from a patient's skin, a substrate configured to hold the sensing element on the patient's skin, and at least two contact probes on the substrate. The contact probes are positioned on the substrate such that galvanically contact the patient's skin when the substrate is fully attached against the patient's skin. A controller is configured to measure impedance between the at least two contact probes and determine whether the substrate has lifted from the patient's skin based on the impedance.

12 Claims, 6 Drawing Sheets

PHYSIOLOGICAL SENSOR AND SENSING METHOD WITH SENSOR LIFT DETECTION

BACKGROUND

The present disclosure generally relates to physiological sensors for detecting a physiological value from a patient, and more specifically to wireless physiological sensors attachable to a patient's skin incorporating systems and methods for detecting when a sensor has lifted from a patient's skin.

In the field of medicine, physicians often desire to monitor multiple physiological characteristics of a patient. Often patient monitoring involves the use of several sensors attached to the patient. The sensors may remain attached for long treatment periods, such as days or weeks. Several different types of physiological monitoring is often performed, such as pulse oximetry, blood pressure monitoring, heart beat and/or electrocardiograph (ECG) waveform monitoring, temperature monitoring, etc. Each type of physiological monitoring requires attachment of a physiological sensor or sensors to the patient. In some embodiments, each physiological sensor is connected by a wire or cable to a patient monitor. In other embodiments, one or more of the physiological sensors are wireless, each having a wireless communication link established with a patient monitor, hub, or other host device or network.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a physiological sensor includes a sensing element to detect physiological information from a patient's skin, a substrate configured to hold the sensing element on the patient's skin, and at least two contact probes on the substrate. The contact probes are positioned on the substrate such that they are in galvanic contact with the patient's skin when the substrate is fully contacting the patient's skin. A controller is configured to measure impedance between the at least two contact probes and determine whether the substrate has lifted from the patient's skin based on the impedance.

A method of measuring temperature from the patient with a temperature sensor includes providing a temperature sensor having a temperature sensing element to detect temperature from a patient's skin and at least two contact probes on opposing sides of the temperature sensing element. The contact probes are positioned to be in galvanic contact with the patient's skin when the temperature sensor is fully contacting or fully attached to the patient's skin. The method of measuring temperature further includes measuring, with the temperature sensing element, a temperature of the patient and measuring impedance between the at least two contact probes. A controller determines whether the substrate has lifted from the patient's skin based on the impedance. If the substrate has not lifted from the patient's skin, the temperature measurement is transmitted. If the substrate has lifted from the patient's skin, a sensor off alert is generated.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
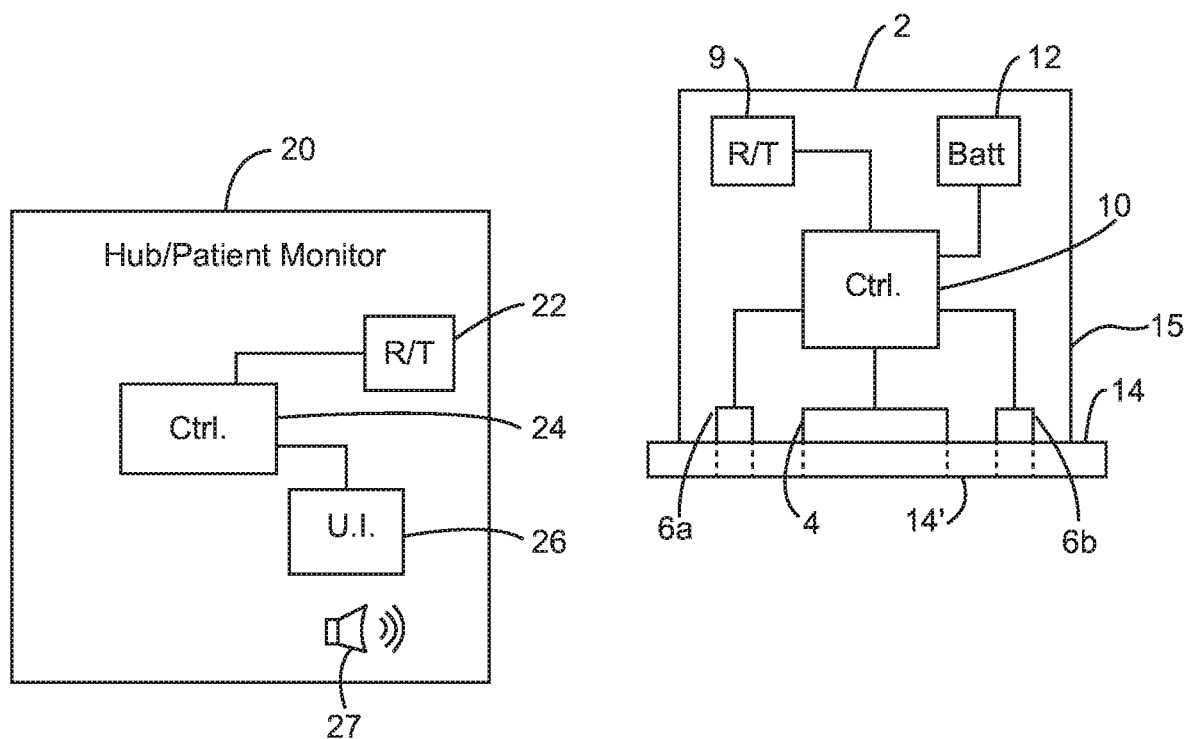
FIG. 1 provides a schematic diagram of one embodiment of a physiological sensor in wireless communication with a hub or host patient monitor, wherein the physiological sensor includes lift detection systems and methods according to one embodiment of the present disclosure.

Monitoring plays a critical role in patient care. The present inventor has recognized that problems exist with physiological sensors where the physiological measurements become inaccurate due to sensor lift, or partial detachment of the sensor from the patient's skin. In certain types of physiological parameter measurements, it is not easy or even possible to detect that the physiological sensor is not collecting accurate physiological data based on the physiological data, alone. One example is in temperature measurement, where a continuously measured temperature may slowly begin to drift as a sensor becomes partially lifted, or detached, from the patient's skin. However, the slow drift due to sensor detachment may be difficult or impossible to distinguish from the slow drift in the patient's actual body temperature.

This problem with inaccurate temperature measurement due to sensor lift commonly presents itself in neonatal patient monitoring. Maintaining appropriate body temperature of a neonate, particularly a premature neonate housed in an incubator or warmer, relies on accurate temperature measurements from the neonate. A problem exists in neonatal care where a temperature sensor becomes partially lifted from the neonate's skin and an inaccurate temperature is measured from the patient. Typically when sensor lift occurs, the temperature measurements are lower than the neonate's actual body temperature because the air surrounding the neonate is at a lower temperature than the body temperature. These inaccurately low body temperature measurements from the neonate cause a temperature control system within the incubator or warmer to inappropriately increase the temperature of the microenvironment within the infant care device. This can cause hyperthermia for the infant, which can be dangerous if an intervention is not effectuated.

The inventor has also recognized problems due to sensor lift in other types of physiological monitoring, including SPO2 monitoring and respiration monitoring, to name a few. For example, the inventor has recognized that SpO2 sensors that are not sufficiently attached to a patient, such as the patient's finger or foot (a common measurement location for neonates) resulting in inaccurately low SpO2 measurements. Similarly, insufficient attachment of surface electrodes, or sensors, to a patient's skin can cause inaccurate respiration rate measurements. In both instances, the inaccuracy of these measurements may not be immediately detectable based on the physiological measurement and may be indistinguishable from an actual low reading.

In view of the foregoing problems and challenges in the relevant art of physiological monitoring, the inventor has developed the disclosed system and method that incorporates lift detection to detect when the physiological sensor is not properly attached to the patient's skin. Each physiological sensor comprises two or more contact probes positioned in galvanic contact with the patient's skin when the sensor is properly attached to the patient. For example, one or more pairs of contact probes may be positioned on opposing sides of the sensing element and impedances are measured between the contact probes such that the impedance measurement region crosses the sensing element. The impedance measurements can then be used to determine whether the sensor is fully contacting the patient's skin. Various numbers and placement of the contact probes may be provided as discussed further herein.

FIG. 1 depicts one embodiment of a physiological sensor 2 having two contact probes 6a and 6b positioned on opposite sides of the sensing element 4. The sensing element 4 and contact probes 6a, 6b are arranged on a substrate 14. In the depicted example, the physiological sensor is a wireless physiological sensor having a wireless transmitter 9 or transceiver that communicates the recorded physiological parameter values and other information to a hub or patient monitor 20, or other device configured to receive the physiological measurements (herein after hub 20). In various embodiments, the hub 20 may be a device incorporated into a larger patient care system such as an incubator or warmer, or a multi-parameter patient monitor receiving physiological information from multiple different types of sensing devices. The hub 20 may include a controller 24, which may be configured to process and/or display physiological data recorded by the sensor 2. The hub 20 may include a user interface 26, such as for displaying the physiological information recorded by the sensor 2. The user interface may include a display device and may also include one or more speakers 27 or buzzers for generating an audio alert.

The wireless physiological sensor 2 shown in FIG. 1 includes a sensor module 15 mounted on the substrate 14 and housing a controller 10, transmitter 9 (which may be a transceiver), and a battery 12 to power the wireless sensor. The sensor module 15 may comprise a housing that is attached to the substrate 14. In certain embodiments, the sensor module 15 may be reusable and the substrate 14 containing the sensing element 4 and two or more contact probes 6a, 6b may be disposable. In other embodiments, the entire physiological sensor 2 may be disposable or may be reusable.

The controller 10 receives physiological information detected by the sensing element 4. The sensing element 4 may be any type of device for sensing or detecting physiological information from the patient, which may include but is not limited to a skin electrode, temperature sensor, pressure sensor, flow sensor, infrared or other pulse oximetry sensor, or the like. The controller 10 is configured to receive and process the physiological information from the sensing element 4, such as to filter and digitize the information, as well as to process the digital signal to extract relevant physiological values therefrom. The controller 10 may include a processor as well as signal processing elements, including filters, amplifiers, or the like as is required or appropriate for processing the type of physiological information that the sensing element 4 is configured to detect.

The transmitter 9 is configured to communicate the physiological information to the hub 20 by a wireless communication means, which may include any appropriate wireless communication protocol. In one embodiment, the hub 20 is also configured to communicate information to the sensor, and thus is configured with a transceiver 22 that communicates with a transceiver 9 in the physiological sensor 2. In one embodiment, the transceiver 22 is configured as a body area network with one or more transceivers 9 in one or more physiological sensors 2 on the patient. In other embodiments, the physiological sensor 2 and hub 20 may communicate by other radio protocols, such as but not limited to Bluetooth, Bluetooth Low Energy (BLE), ANT, and Zigbee. In other embodiments, the physiological sensor 2 may be a wired sensor, rather than a wireless sensor, wherein communication of the physiological information and/or the sensor off alert as described above, are transmitted to the hub 20 by a standard lead wire or other wired connection there between.

Two or more contact probes 6a, 6b are connected to the controller 10 and the controller is configured to determine an impedance there between. When the sensor 2 is properly attached to the patient's skin, then the impedance between the contact probes 6a and 6b will be a skin impedance measurement. In certain embodiments, a separate impedance measurement device may be provided apart from the controller 10 and communicate the skin impedance to the controller 10, which may then determine whether sensor lift has occurred. For example, the skin impedance may be determined by applying a voltage across the probe pair 6a-6b and calculating the impedance based on the measured current. Various other methods of determining impedance, particularly skin impedance between electrodes, is known and may utilized.

The sensing element 4 and contact probes 6a, 6b are arranged on a substrate 14 which is configured to hold the sensing element 4 and contact probes 6a, 6b such that they can contact the patient's skin. The type and form of substrate 14 used will vary depending on the sensor type. Where the physiological sensor 2 is adhered to the patient's skin by an adhesive, the substrate 14 may have an adhesive on the bottom side 14'. For example, the substrate 14 may be a foam or plastic material having a conductive skin adhesive on the bottom side 14', as is standard for many types of skin electrodes. The sensing element 4 and contact probes 6a, 6b are positioned in the substrate material such that they penetrate through the substrate material and are able to electrically connect between the patient's skin and/or conductive adhesive connected to the patient's skin and the controller 10 or other element receiving the signals measured therefrom. In other embodiments, the physiological sensor 2 may be maintained against the patients by other means other than adhesive, such as strapped or clipped to the patient's skin. For example, the sensor 2 may be an SpO2 sensor and may include a standard finger clip configured to press the sensing element 4, which would be a detector, against the patient's skin. In still other embodiments, the physiological sensor 2 may be adhered to the patient by a strap or band. For example, a physiological sensor 2 configured as a respiration sensor may be positioned on a strap that goes around a patient's chest.

The probes 6a and 6b are positioned in the substrate to measure whether the sensing element is in good contact with the skin and help ensure that physiological measurements are accurately obtained. Namely, the two or more probes 6a and 6b are positioned such that impedance measurements between the probes 6a, 6b can be used to detect whether the substrate on which the sensing element 4 is positioned is lifting off of the patient's skin. The probes 6a, 6b are configured and positioned to detect when the substrate has lifted from the patient's skin, and preferably before the sensing element 4 lifts from the patient's skin thus the accuracy of the physiological measurement is impacted.

In one embodiment, sensor lift is detected when the impedance between any subset of the two or more contact probes 6a, 6b exceeds a threshold impedance. In another embodiment, sensor lift may be detected when a difference between two contemporaneously determined impedances between pairs of contact probes differ by a predetermined amount. The latter method requires at least three contact probes 6 on the sensor, wherein the at least three contact probes form at least two pairs between which impedance can be measured, and thus at least two impedance measurements. The at least two impedance measurements can then be compared to one another. In latter method is adaptable to any skin condition, type, placement location, etc. because the measurements are compared to one another rather than to an absolute threshold. Since the contact probes are located in a relatively small area, it is expected that the impedance measurements between equally spaced, or at least similarly spaced, contact probes 6a, 6b will be very similar to one another. Therefore, the impedance measurements between different pairs of contact probes can be compared to one another and if greater than a threshold difference exists, it can be assumed that the substrate has lifted from the patient's skin such that at least a portion of the substrate is no longer fully adhered to or otherwise fully contacting the patient's skin.

In certain embodiments, the controller 10 may be configured to transfer a sensor alert once it detects that the substrate has lifted from the patient's skin. The sensor off alert may be, for example, a message transmitted from the physiological sensor 2 to the hub 20 or other receiving device. The hub 20 may then be configured to generate a visual and/or audio alert via the user interface 26, 27 thereon. Alternatively or additionally, the sensor 2 may include an on-board alert device, such as an LED that is illuminated to indicate the sensor off condition or a buzzer configured to generate an audio alert upon detection of the sensor off condition.

Figure 2:
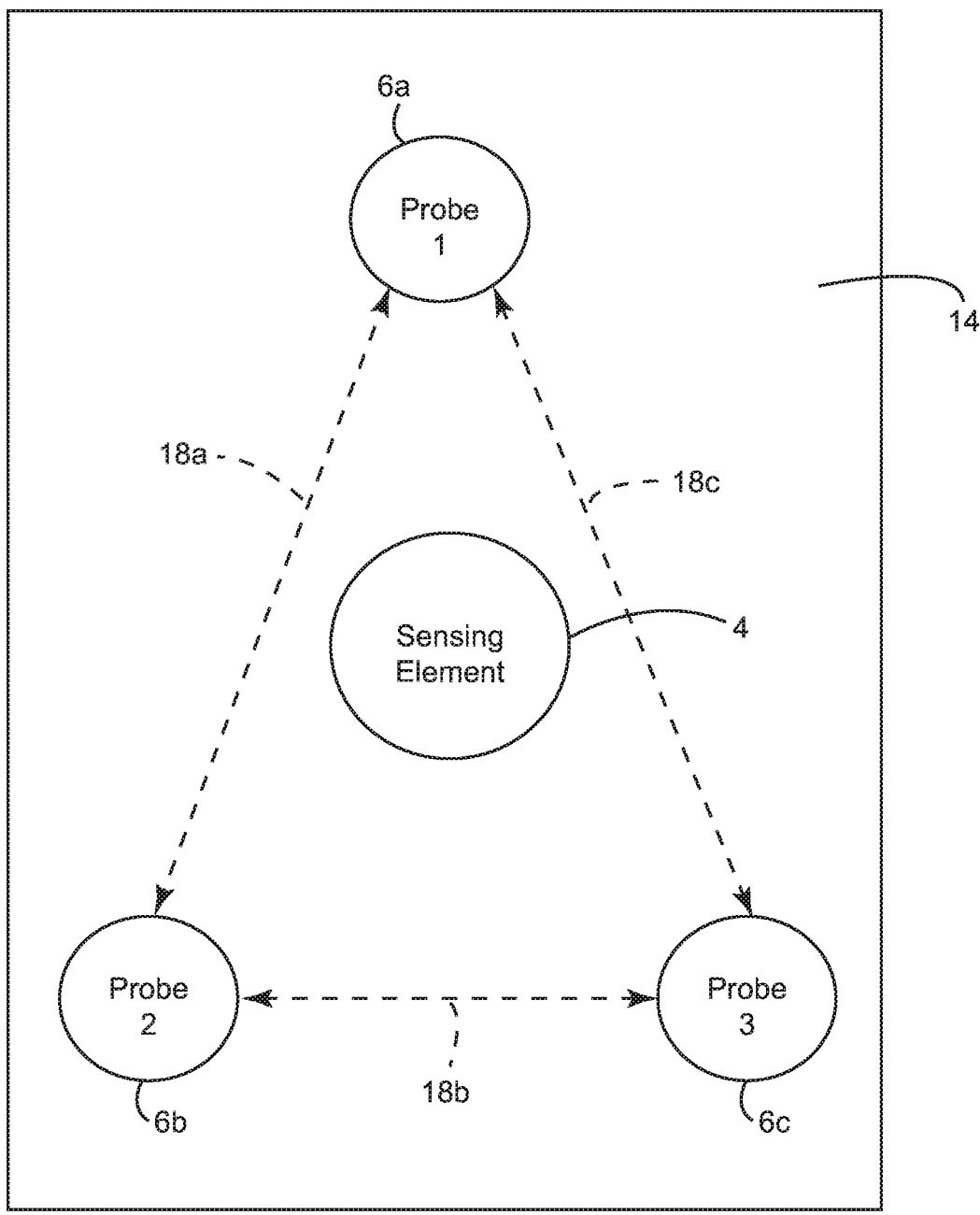
FIG. 2 depicts one embodiment of a physiological sensor having conductive probes and lift detection according to the present disclosure.

Various probe arrangements are possible and within the scope of the present disclosure, examples of which are provided herein. In one embodiment, two probes 6a, 6b may be positioned on either side of a sensing element 4, such as illustrated in FIG. 1. In other embodiments, three, four, or more probes 6 may be incorporated. FIG. 2 depicts an exemplary embodiment of a sensor device 2 comprising three contact probes 6a-6c. Three contact probes 6a-6c are positioned around the sensing element 4 and on the substrate 14. Impedance measurements are made between pairs of the contact probes 6a-6c along impedance paths 18a, 18b, and 18c. Thus, three impedance measurements are performed between three pairs of contact probes-6a-6b, 6b-6c, and 6c-6a. If, for example, a corner of the substrate 14 were to lift, at least one of the impedance measurements 18a-18c would increase.

In an embodiment where the lift detection is performed based on a threshold impedance, one or more of the impedance measurements would exceed threshold once lift begins to occur. In an embodiment where a comparative analysis is performed, a difference between each of the impedances 18a, 18b, and 18c is performed. If any of the differences exceed a predetermined threshold difference, then lift is detected.

Figure 3:
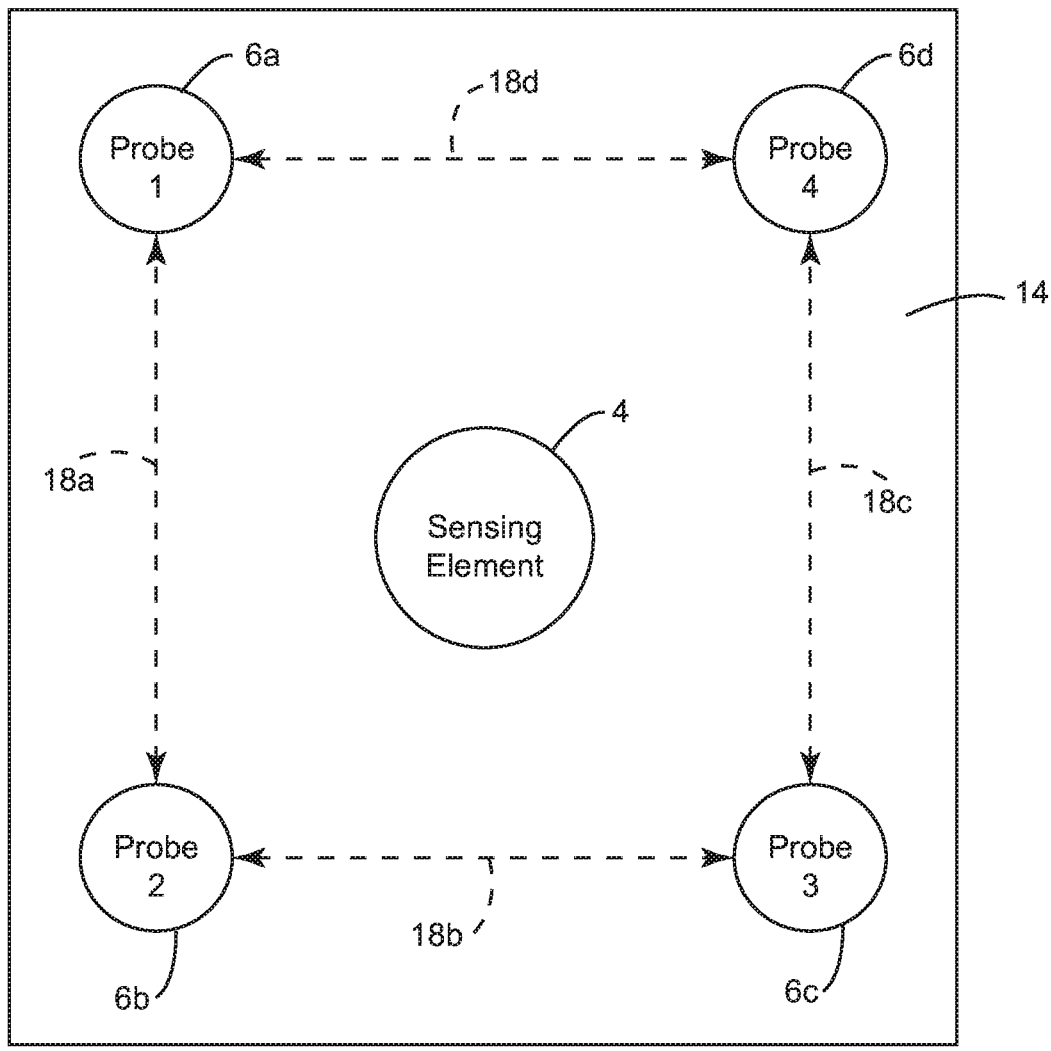
FIG. 3 depicts a physiological sensor having conductive probes and lift detection according to another embodiment of the present disclosure.

FIG. 3 depicts an embodiment comprising four contact probes 6a-6d. In the depicted example, the sensor is configured to perform four impedance measurements along four impedance paths 18a-18d four pairs of contact probes 6a-6b, 6b-6c, 6c-6d, and 6d-6a, respectively. The impedance paths 18a-18d between the four pairs of contact probes 6a-6d form a perimeter around the sensing elements such that impedance measurements are performed at various points surrounding the sensing element 4. In other embodiments, alternative or additional impedance paths may be formed between the four contact probes 6a-6d.

Figure 4:
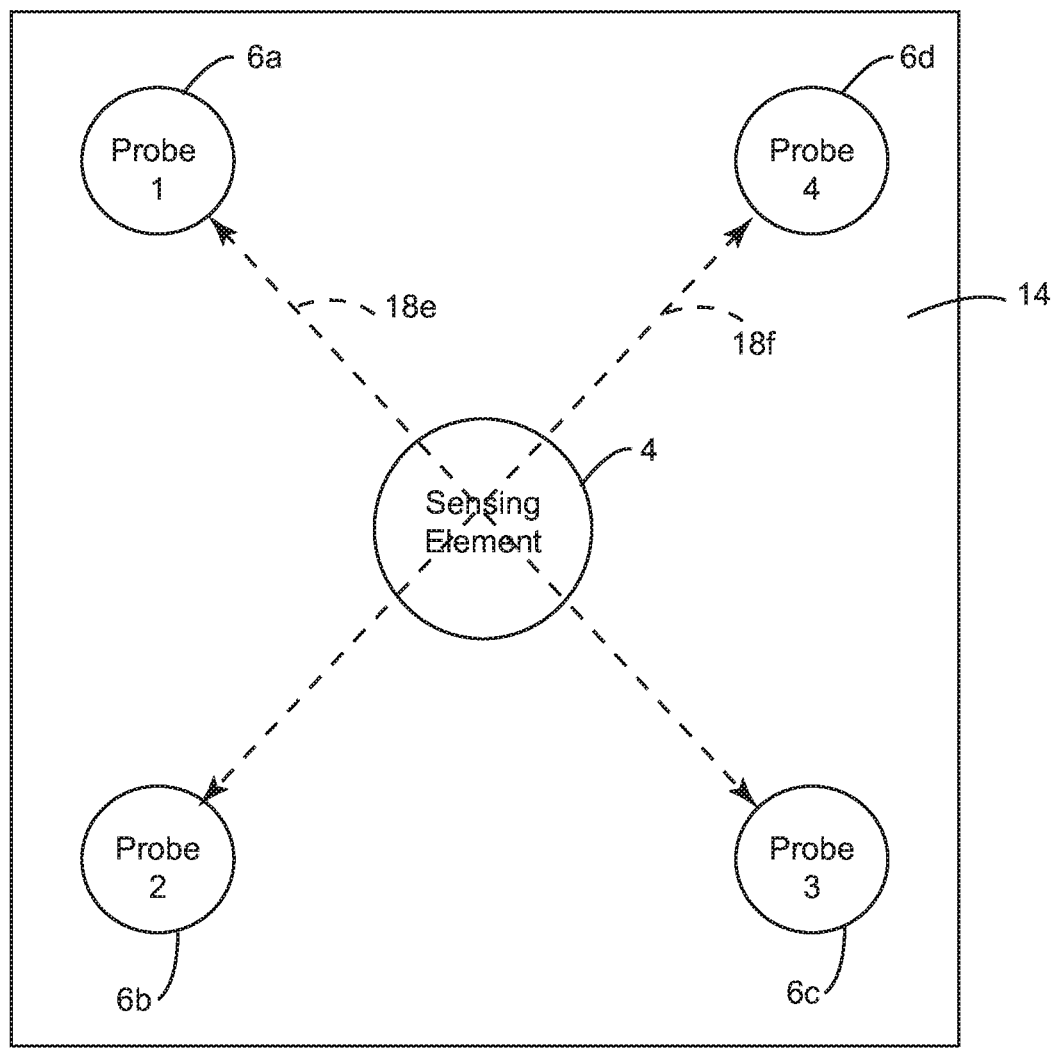
FIG. 4 depicts a physiological sensor having contact probes and lift detection according to another embodiment of the present disclosure.

FIG. 4 depicts impedance paths along diagonals between the four contact probes 6a-6d. In FIG. 4, the sensor is configured to perform two impedance measurements between the four contact probes 6a-6d, thus utilizing two pairs of contact probes. In such an embodiment, the two impedances are measured across the sensing element 4, and in the depicted example the impedance paths 18e and 18f run on a diagonal through the sensing element 4. In certain embodiments, a sensor 2 may be configured to measure six impedances based on the depicted four contact probes 6a-6d, and thus to perform impedance measurements along each of the impedance paths 18a-18f depicted in both FIGS. 3 and 4.

Figure 5:
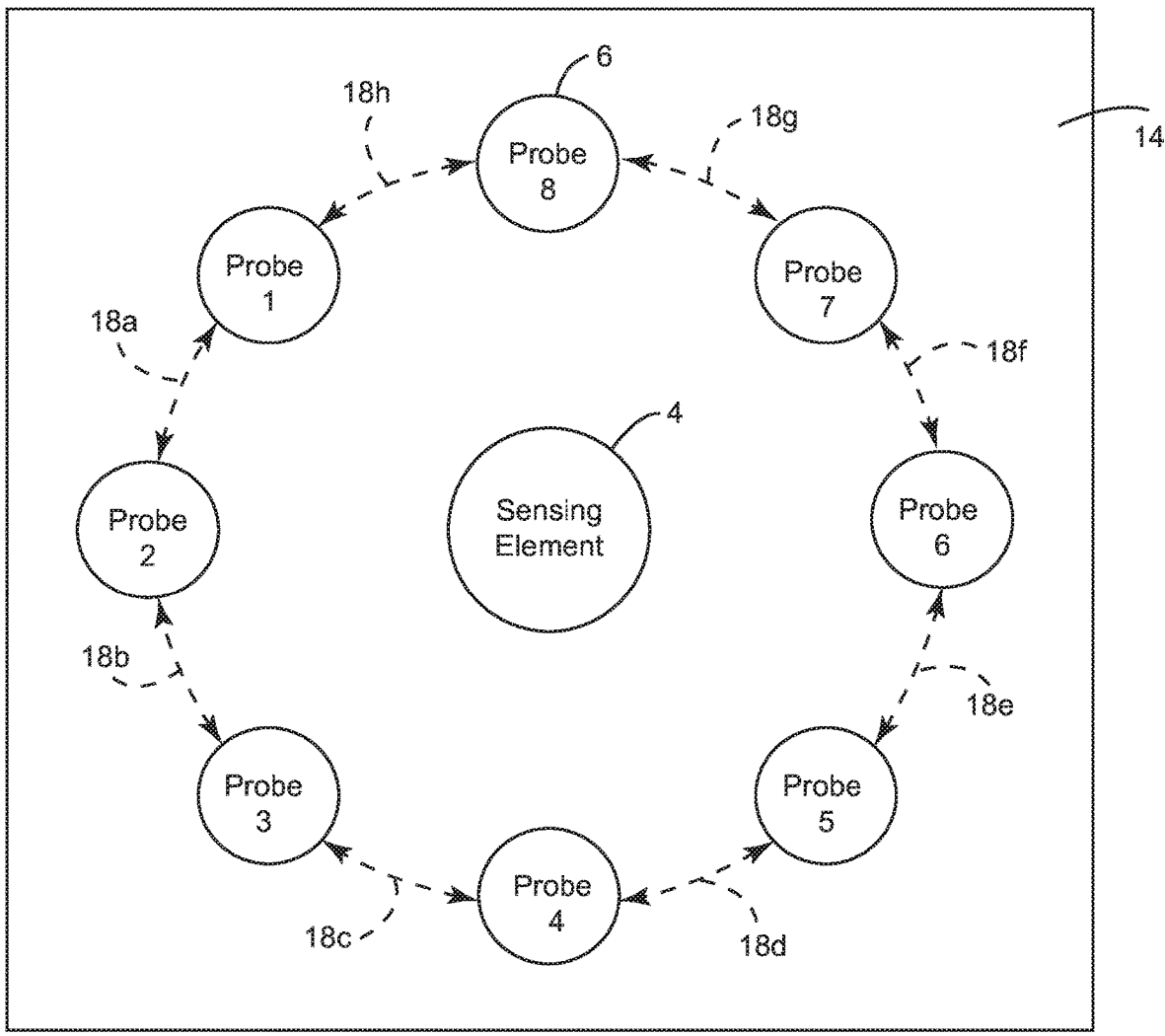
FIG. 5 depicts a physiological sensor having contact probes and lift detection according to another embodiment of the present disclosure.

Any number of contact probes 6 may be incorporated into the physiological sensor 2 and mounted on the substrate 14. FIG. 5 depicts an exemplary embodiment providing eight contact probes, six surrounding the sensing element 4. The probes 6 are arranged in eight pairs for impedance measurement purposes, and impedances are measured along eight paths 18a-18h surrounding the sensing element 4. In the depicted example, the eight impedance measurements form a perimeter around the sensing element 4. In other embodiments, the contact probe 6 could be arranged in four pairs such that the impedance paths travel across the sensing element 4.

Figure 6:
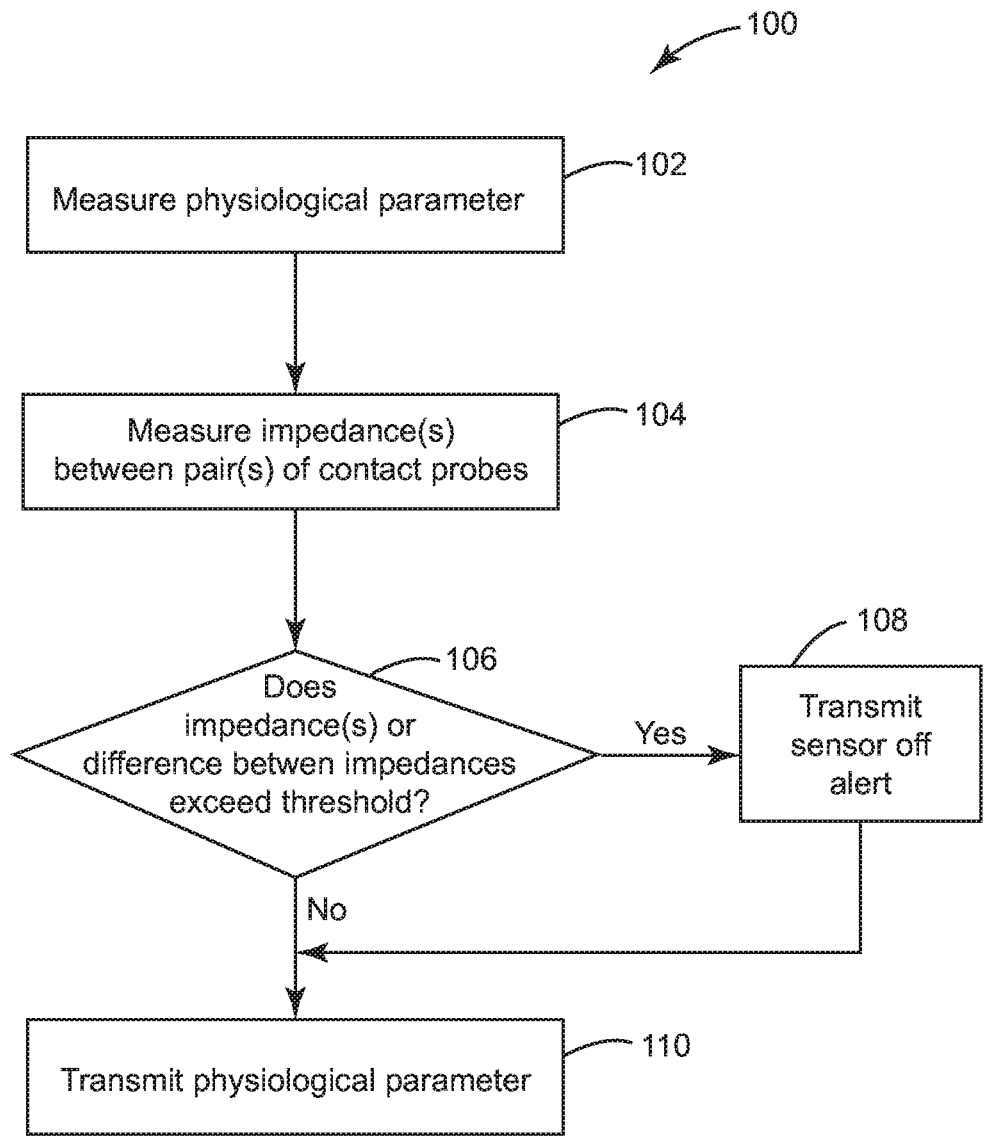
FIG. 6 depicts one embodiment of a method of lift detection and physiological parameter measurement according to one embodiment of the present disclosure.

FIG. 6 depicts one embodiment of a method 100 of measuring a physiological parameter from a patient, such as measuring temperature. The physiological parameter is measured at step 102 based on physiological information collected by the sensing element 4. The impedances between pairs of contact probes 6 are determined at step 104. Steps 102 and 104 may be conducted, for example, by a single controller 10 in the physiological sensor 2. In other embodiments, steps 102 and 104 may be executed by separate controllers within the physiological sensor 2.

Logic is then executed at step 106 to determine whether a relevant threshold is exceeded. As described above, in one embodiment, logic is executed to determine whether any impedance measurement exceeds an impedance threshold. In another embodiment, one or more impedance measurements are compared to one another to determine whether a difference between any of the at least two measured impedances is greater than a threshold difference. In certain embodiments, the logic of step 106 is performed by the controller 10, which stores and executes corresponding software instructions. If the relevant threshold is exceeded at step 106, then a sensor off alert is transmitted at step 108. As described above, the sensor off alert may be a message transmitted from the physiological sensor 2 to the hub 20. In another embodiment, the sensor off alert may be a visual or auditory alert generated by the physiological sensor 2, such as by a light indicator and/or buzzer incorporated therein. In certain embodiments, the physiological parameter may still be transmitted through the physiological sensor 2 to the hub 20, even when the sensor off alert is generated. In other embodiments, the physiological parameter may not be transmitted and only the sensor off alert may be generated. If the impedance does not exceed the threshold of step 106, then the physiological parameter is transmitted at step 110 and physiological monitoring continues.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A physiological sensor comprising:
   a sensing element to detect a physiological information from a patient's skin, wherein the sensing element is one of a temperature sensor, a pulse oximetry sensor, flow sensor, pressure sensor, or a respiration sensor;
   a substrate configured to hold the sensing element on the patient's skin;
   a plurality of contact probes arranged around the sensing element on the substrate, wherein the contact probes are positioned on the substrate such that they are in galvanic contact with the patient's skin when the substrate is fully contacting the patient's skin;
   a controller configured to measure impedance along impedance paths between the plurality of contact probes and determine whether the substrate has lifted from the patient's skin based on the impedance; and
   wherein at least one impedance path extends between contact probes on opposite sides of the sensing element such that the at least one impedance path extends across the sensing element.

2. The physiological sensor of claim 1, wherein the controller is configured to determine that the substrate has lifted from the patient's skin if the impedance exceeds a threshold impedance.

3. The physiological sensor of claim 1, wherein the controller is furthered configured to transmit a sensor off alert if the substrate has lifted from the patient's skin.

4. The physiological sensor of claim 3, wherein the physiological sensor is a wireless sensor further comprising a wireless transmitter, and wherein the controller is further configured to operate the wireless transmitter to transmit the sensor off alert.

5. The physiological sensor of claim 4, wherein the sensing element is the temperature sensor and the physiological information is skin temperature, and wherein the physiological sensor is a wireless temperature sensor configured to measure temperature of an infant, and wherein the wireless temperature sensor is configured to transmit the sensor off alert to an infant care device housing the infant.

6. The physiological sensor of claim 1, wherein the plurality of contact probes comprises at least three contact probes, and wherein the controller is configured to measure at least two impedances along respective impedance paths between the at least three contact probes.

7. The physiological sensor of claim 6, wherein the controller is further configured to determine a difference between each of the at least two measured impedances, wherein the controller is configured to determine that the substrate has lifted from the patient's skin if the difference between any of the at least two measured impedances exceeds a threshold difference.

8. The physiological sensor of claim 1, wherein the plurality of contact probes comprises at least three contact probes, and wherein the controller is configured to measure at least three impedances along respective impedance paths between at least three pairs of contact probes formed by the at least three contact probes.

9. The physiological sensor of claim 8, wherein the at least three pairs form a perimeter around the sensing element.

10. The physiological sensor of claim 1, wherein the plurality of contact probes comprises at least four contact probes, and wherein the controller is configured to measure at least two impedances along respective impedance paths between at least two pairs of contact probes formed by the at least four contact probes.

11. The physiological sensor of claim 10, wherein the at least two impedances are measured between contact probes on opposite sides of the sensing element such that the at least two impedances are measured across the sensing element.

12. The physiological sensor of claim 1, wherein the plurality of contact probes comprises at least four contact probes, and wherein the controller is configured to measure at least four impedances along respective impedance paths between at least four pairs of contact probes formed by the at least four contact probes, wherein the at least four pairs form a perimeter around the sensing element.

* * * * *